US009839661B2

(12) United States Patent
Ruden et al.

(10) Patent No.: US 9,839,661 B2
(45) Date of Patent: Dec. 12, 2017

(54) PLANT MATERIAL DRYING METHODS

(75) Inventors: Susan Ruden, Dexter, IA (US);
Brindha Narasimhamoorthy, West Des Moines, IA (US); John A. Greaves, Ankeny, IA (US); Sarah Wildgen, Overland Park, KS (US)

(73) Assignee: KEMIN INDUSTRIES, INC., Des Moines, IA (US)

( * ) Notice: Subject to any disclaimer, the term of this patent is extended or adjusted under 35 U.S.C. 154(b) by 1019 days.

(21) Appl. No.: 13/104,498

(22) Filed: May 10, 2011

(65) Prior Publication Data
US 2011/0277337 A1   Nov. 17, 2011

Related U.S. Application Data

(60) Provisional application No. 61/333,403, filed on May 11, 2010.

(51) Int. Cl.
*F26B 3/34* (2006.01)
*A61K 36/534* (2006.01)
*A23L 33/105* (2016.01)

(52) U.S. Cl.
CPC .......... *A61K 36/534* (2013.01); *A23L 33/105* (2016.08)

(58) Field of Classification Search
CPC ......... F26B 3/34; A61K 36/53; A61K 36/534; A01N 65/22
USPC ........... 34/259, 255, 245, 246, 266; 424/747
See application file for complete search history.

(56) References Cited

U.S. PATENT DOCUMENTS

| 4,045,639 | A | * | 8/1977 | Meisel ........................ 219/700 |
| 4,430,806 | A | * | 2/1984 | Hopkins ................. A23B 9/04 219/700 |
| 5,105,563 | A | * | 4/1992 | Fingerson ............ A01D 43/003 34/203 |
| 5,338,765 | A | * | 8/1994 | Near et al. .................... 521/50.5 |
| 5,956,865 | A | * | 9/1999 | Durance et al. ................ 34/265 |
| 6,128,831 | A | * | 10/2000 | Durance ............. F26B 11/0495 34/263 |
| 6,312,745 | B1 | | 11/2001 | Durance et al. |

(Continued)

FOREIGN PATENT DOCUMENTS

| CN | 1544023 A | * | 11/2004 |
| CN | 1301654 C | | 2/2007 |

(Continued)

OTHER PUBLICATIONS

Maryam Shekarchi et al., Comparative study of rosmarinic acid content in some plants of Labiatae family, Jan. 2012, Pharmacogn Magazine, p. 37-41.*

(Continued)

*Primary Examiner* — John McCormack
(74) *Attorney, Agent, or Firm* — Nyemaster Goode P.C.

(57) ABSTRACT

A method of drying fresh plant material wherein the fresh plant material containing a desired heat labile compound is exposed to microwave energy at an intensity and for a time sufficient to remove a majority of the water from the plant material without degrading a majority of the heat labile compound. The method is particularly suited to in-field drying of freshly harvested plant material to reduce the weight and volume of the plant material for savings transportation costs to an extraction facility while preserving at high levels the amount and activity of the desired heat labile compound.

22 Claims, 3 Drawing Sheets

RA content and relative water loss as a function of drying time using a microwave

(56) References Cited

U.S. PATENT DOCUMENTS

| | | | |
|---|---|---|---|
| 7,001,629 B1* | 2/2006 | Mengal et al. | 426/241 |
| 2002/0088137 A1* | 7/2002 | Savarese | 34/266 |
| 2003/0150128 A1 | 8/2003 | Macaluso et al. | |
| 2006/0034981 A1 | 2/2006 | Pan et al. | |
| 2008/0152733 A1 | 6/2008 | Logsdon | |
| 2009/0317523 A1* | 12/2009 | Hirschberg | A23B 7/022 426/241 |
| 2010/0137433 A1* | 6/2010 | Kott | A61K 36/534 514/532 |

FOREIGN PATENT DOCUMENTS

| | | | |
|---|---|---|---|
| CN | 101513244 | 8/2009 | |
| EP | 0398798 A2 * | 11/1990 | C11B 9/025 |
| JP | 59-213356 A | 12/1984 | |
| KR | 10-2009-0105739 A | 10/2009 | |

OTHER PUBLICATIONS

Bousbia et al., "Comparison of Two Isolation Methods for Essential Oil from Rosemary Leaves", "Food Chemistry", May 2009, pp. 355-362, vol. 114, No. 1.

Lucchesi et al., "Solvent-free microwave extraction of essential oil from aromatic herbs: comparison with conventional hydro-distillation", "Journal of Chromotography", Jul. 23, 2004, pp. 323-237, vol. 1043, No. 2, Publisher: Publishers B.V.

Presti et al., "A Comparison between different techniques for the isolation of rosemary essential oil", "Journal of Separation Science", Feb. 2005, pp. 273-280, vol. 28, No. 3.

Proestos, et al., "Application of Microwave-assisted Extraction to the Fast Extraction of Plant Phenolic Compounds", "Food Science and Technology", Jan. 14, 2008, pp. 652-659, vol. 41, No. 4, Publisher: Academic Press, Published in: United Kingdom.

Vian et al., "Microwave hydrodiffusion and gravity, a new technique for extraction of essential oils", "Journal of Chormotography", May 2008, pp. 14-17, vol. 1190, No. 1-2, Publisher: Elsevier Science Publishers B.V.

Figel et al. Effects of drying on quality of rosemary: reduction of volatile compounds. Journal Alimentacion, Equipos y Tecnologia 2009 No. 247 pp. 44-47.

Arslan et al. Evaluation of drying methods with respect to drying kinetics, mineral content and colour characteristics of rosemary leaves. Energy Conversion and Management vol. 49, Issue 5, May 2008, pp. 1258-1264.

Ozbet et al. Thin-layer drying characteristics and modelling of mint leaves undergoing microwave treatment. Journal of Food Engineering vol. 83, Issue 4, Dec. 2007, pp. 541-549.

Tsubaki et al. Microwave Heating of Tea Residue Yields Polysaccharides, Polyphenols, and Plant Biopolyester. J. Agric.Food Chem., 2008, 56(23), pp. 11293-11299.

Chan et al. Antioxidant activity of Camellia sinensis leaves and tea from a lowland plantation in Malaysia. Food Chemistry vol. 102, Issue 4, 2007, pp. 1214-1222.

Fletcher, R.S., et al., Novel Mentha Spicata clones with enhanced rosmarinic acid and antioxidant activity. 2005, Proc. WOCMAP III, vol. 6: Traditional Medicine and Nutraceuticals Ada Horticulture, 6S0, ISHS. pp. 31-40.

Fletcher, RS, et al., Heat stress reduces the accumulation of rosmarinic acid and the antioxidant activity of Spearmint (*Mentha spicata* L). 2005, Journal of Science of Food and Agriculture. 85:2429-2436.

Mazumder, A., et al., Curcumin analogs with altered potencies against HIV-1 integrase as probles for biochemical mechanisims of drug actions. 1997, Journal of medical Chemistry. 40:3057-3063.

Szabo, E., et al., Fungal elicitor preparations and methyl jasmonate enhance rosmarinic acid accumulation in suspension cultures of Coeus Blumei. 1999, Plant Cell Reports. 18:485-489.

Hooker, C.W., et al., Inhibitors of human immunodeficiency virus Type 1 reverse trancriptase target distinct phases of early reverse transcription. 2001, Journal Virology. 75:3095-3104.

Bouraout, M., et al., Microwave and convective drying of potato slices. 1994, Journal of Food Process Engineering. 17:353-363.

Tulasidas, T.N., et al., Modelling of microwave drying of grapes. 1997, Canadian Agricultural Engineering. 39:57-67.

Funebo, T., et al., Microwave-assisted air dehydration of apple and mushroom. 1998, Journal of Food Engineering. 38(3):353-367.

Vadivambal, D.S., et al., Changes in the microwave treated agricultural products—a review. 2007, Biosystems Engineering. 28:1-16.

Parminder, K, et al., Influence of different drying techniques on quality of spearmint (*Mentha spicata* L.). 2009, Journal of Food Science and Technology. 46(5): 440-444.

Balladin, D.A., et al., Evaluation of solar dried thyme (*Thymus vulgaris* L.) herbs. 1999, Renewable Energy. 17:523-531.

Venskutonis, P.R., et al., Influence of drying and irradiation on the composition of the volatile compounds of thyme (*Thymus vulgaris* L.). 1996, Flavour and Fragrance Journal. 11:123-128.

* cited by examiner

PLANT MATERIAL DRYING METHODS

This application claims priority to U.S. Patent Application Ser. No. 61/333,403, filed May 11, 2010.

BACKGROUND OF THE INVENTION

The invention relates generally to drying of plant material and, more specifically, to a novel, non-obvious process for drying of plant material to maintain a high content of a labile bio-active molecule.

Rosmarinic acid (RA) is an ester of caffeic acid and 3,4-dihydroxyphenylacetic acid. It is also a secondary metabolite of various plant species including those of Lamiaceae. Spearmint (*Mentha spicata* L.) is particularly known as a major source of carvone-rich essential oil for perfumery and flavoring industries and is grown worldwide. It is a fast growing perennial that can biosynthesize significant amounts of RA and other phenolics when selected to do so (Fletcher R S, McAuley C and Kott L S. 2005a. Novel *Mentha Spicata* clones with enhanced rosmarinic acid and antioxidant activity. Proc. WOCMAP III, Vol. 6: *Traditional Medicine and Nutraceuticals Ada Horticulture.* 6S0, ISHS. pp 31-40 SA-08-06337; Fletcher R S, McAuley C and Kott L S. 2005b. Heat stress reduces the accumulation of rosmarinic acid and the antioxidant activity of Spearmint (*Mentha spicata* L.). *Journal of Science of Food and Agriculture* 85:2429-2436 SA-09-06343). There is an interest in developing products based on the more polar RA extracted from spearmint that will likely have greater antioxidative efficacy than carnosic acid in beverages, sauces, and emulsions. In addition, this molecule is known to have unique properties including antiviral, antibacterial, and anti-inflammatory activities (Mazumder A, Neamati N, Sunder S, Schulz J, Pertz H, Eich E, and Pommier Y. 1997. Curcumin analogs with altered potencies against HIV-1 integrase as probles for biochemical mechanisms of drug action. *Journal of medical Chemistry.* 40:3057-3063; Szabo E, Thelen A and Paterson M. 1999. Fungal elicitor preparations and methyl jasmonate enhance rosmarinic acid accumulation in suspension cultures of Coleus Blumei. *Plant Cell Reports* 18: 485-489; Hooker C W, Lott W B and Harrich D. 2001. Inhibitors of human immunodeficiency virus Type 1 reverse transcriptase target distinct phases of early reverse transcription. *Journal Virology.* 75: 3095-3104).

Spearmint like many other herbs is highly seasonal in nature and has high levels of moisture. In order to preserve this highly perishable biomass source, and make it available year round for extraction, a post-harvest technological treatment of tissue such as drying and/or freezing is required. In general, aromatic herbs and spices are the most sensitive to any post harvest processing including drying or freezing techniques which increase the biological deterioration of tissue. Such treatments results in the loss of volatiles and flavors, changes in the color and texture, and decreases in the nutritional value.

Drying is one of the oldest preservation techniques. Natural drying (drying in the shade) and hot air drying are still the most widely used methods. However, these methods have several disadvantages and limitations; for instance, they require relatively long duration and high temperatures for optimum drying. The contact of dried material with hot air causes rapid degradation of important flavor compounds and nutritional substances, as well as color alteration. Another disadvantage of this method is tissue shrinkage, which results in tissue collapse thereby reducing the available biomass. Freeze-drying is a technique by which material is frozen, and then dehydrated under vacuum; a process by which the contained water passes from a frozen to a gaseous state. Although freeze drying is an excellent method from a quality standpoint, the drying process requires more time and specialized equipment, resulting in high energy and capital costs.

Compared to air drying, hot air drying and freeze drying, microwave or hybrid microwave drying techniques (microwave-hot air drying; microwave-freeze drying, microwave-vacuum drying; osmotic pretreatment before combined microwave-hot air drying) can greatly reduce the drying time of the biological materials while maintaining quality. There has been extensive research into microwave drying techniques, particularly on drying fruits and vegetables (Bouraout M, Richard P and Durance T. 1994. Microwave and convective drying of potato slices, *Journal of Food Process Engineering* 17: 353-363; Tulasidas T N, Ratti C and Raghavan G S V. 1997. Modelling of microwave drying of grapes, *Canadian Agricultural Engineering* 39:57-67; Funebo T and Ohlsson T. 1998. Microwave-assisted air dehydration of apple and mushroom, *Journal of Food Engineering* 38 (3):353-367). The introduction of a microwave drying/heating technique which reduces drying time considerably and produces a high-quality end product offers a promising alternative and a significant contribution to the herb processing industry. Although microwave drying is a rapid technique, the tissues are not evenly dried due to the non-uniformity in temperature distribution (Vadivambal D S and Jayas R. 2007. Changes in the microwave treated agricultural products—a review. Biosystems Engineering. 28:1-16).

Vacuum-microwave drying offers an alternative way to improve the quality of dehydrated products. The low temperature and fast mass transfer conferred by vacuum, combined with rapid energy transfer of microwave heating, generates very rapid, low-temperature drying. Due to the absence of air during drying, the structure, color and sensory qualities of products can be better preserved. Vacuum-microwave drying requires a large capital investment but has been successfully used in the dehydration of fruits and vegetables (Vadivamabal et al.).

In a recent study, different drying techniques such as convective drying, sun drying, room air drying and solar drying (using polythene tent dryer) were carried out in spearmint for comparison of rehydration characteristics, color, oil content and drying ratio (Parminder K, Satish K, Sadhana A, Neena C, and Manpreet S. 2009. Influence of different drying techniques on quality of spearmint (*Mentha spicata* L.). *Journal of Food Science and Technology.* 46(5): 440-444). In this study, conventional air dried mint samples had higher oil content compared to convective dried samples, particularly at higher temperatures. Retention of green color was higher in convective dried compared to conventional dried samples at higher temperatures. In a study (Fletcher et al.; 2005b) to understand the effect of heat stress on growing spearmint plants, high temperature drying (80° C.) was found to significantly reduce the total phenolics (up to 87%). This study also indicated that the RA levels were not significantly reduced when tissue was dried at low temperature first (35° C.) followed by high temperature drying.

Several scientific reports exist on improved microwave drying methods for fruits and vegetables in the processing industry (Vadivamabal et al.). However, little information currently exists on direct microwave drying of leafy herbs and among the available reports, as all of them mainly focus on using vacuum-microwave drying technique. The effect of drying methods such as conventional drying, solar drying, oven drying and microwave-vacuum drying on volatile compounds has been investigated in thyme (*Thymus vulgaris* L.), sage, oregano (*Origanum* sp), and rosemary (*Rosmarinus officinalis* L.) (Balladin D A and O. Headley O. 1999. Evaluation of solar dried thyme (*Thymus vulgaris* L.) herbs, *Renewable Energy* 17: 523-531); Venskutonis P R, Poll L and Larsen M. 1996. Influence of drying and irradiation on the composition of the volatile compounds of thyme (*Thymus vulgaris* L.), *Flavour and Fragrance Journal* 11: 123-128;). All of these studies indicated that higher temperatures and long duration of exposure reduced the levels of the essential volatile compounds in these herbs. No scientific reports exist on drying kinetics of spearmints, especially for the purpose of commercial extraction and stability of phenolic compounds by comparing different drying techniques. The ability to rapidly dry leaf biomass while at the same time maintaining optimal levels of the temperature labile target molecule, rosmarinic acid, would be a major breakthrough in the use of this plant species for phytochemical production.

There is, accordingly, an interest in developing a suitable drying process of spearmint biomass which would retain the highest levels of rosmarinic acid. The ideal drying technique would permit early harvest, lighter weight for transportation from multiple locations and less space for long term storage of biomass without deterioration to allow for year-round extraction.

SUMMARY OF THE INVENTION

The invention consists of the controlled use of energy to remove the water from plant material while maintaining a high amount of a heat labile constituent. In a specific example, microwave energy is applied to freshly harvested mint to remove water from the plant material without destroying significant amounts of rosmarinic acid present in the mint. The method permits the rapid and efficient drying of large quantities of plant material, reducing both the weight and volume of the plant material for reduced transport and storage requirements while retaining the heat labile constituent in high amounts for later extraction.

DESCRIPTION OF THE INVENTION

Figure 1A:
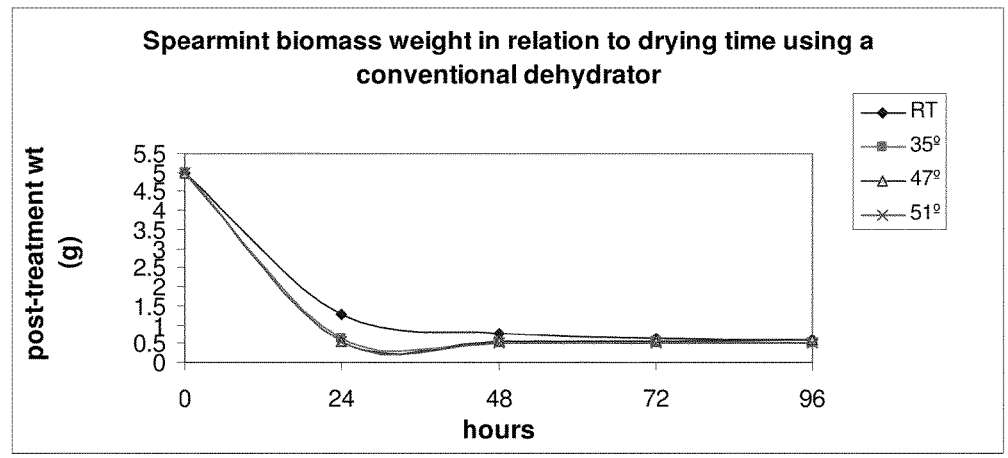
FIG. 1 is a graph of relative water content as a function of drying time using a dehydrator.

Rosmarinic acid (RA) is a potent phenolic antioxidant found in various plant species including spearmint (*Mentha spicata* L.). An effective method for drying spearmint tissue which retains high levels of RA is crucial for viable commercial RA production. A study was conducted to determine the efficiency of three different drying methods of spearmint tissue such as freeze drying, conventional hot air drying and microwave drying. Four different durations of drying using a freeze dryer, twelve different temperature-duration combinations using a conventional dehydrator (hot air drying), and eight different durations of drying using a microwave were tested. The effects of drying methods on relative water content, tissue color and RA levels were evaluated. In a conventional dehydrator and the freeze-dryer, the lowest stable moisture levels (<10%) of dried spearmint tissue were reached at 48 h. On the other hand, a stable moisture level was reached within 2.5 minutes of drying with a microwave. The changes in the RA levels of the tissue were dependent on the method of drying, the duration of drying and the temperature used for drying. Air-dried samples and dehydrator dried samples of spearmint tissue were less green and exhibited lower RA levels compared to microwave dried and freeze-dried samples. The RA levels of tissue that was air-dried at room temperature (RT) or dehydrator dried beyond 48 h decreased as the duration of drying was increased. However, using the dehydrator, at very high temperatures (≥57° C.), the RA levels were reduced by up to 80% at 24 h of drying. The optimum drying time using a microwave at which the highest level of RA retained coupled with the lowest tissue shrinkage was 2.5 minutes. The freeze dried samples retained the highest level of RA irrespective of drying time with the lowest amount of tissue shrinkage compared to all other methods. However, microwave drying seems to be the most efficient way of drying spearmint tissue in a short time with retention of high RA levels, desirable tissue color and density.

While microwave energy is used in a preferred embodiment of the present invention, the invention includes the use of other types of energy and processes that would also achieve the objectives of drying fresh plant material while retaining an economical amount of a labile compound present in the plant material. For example, infrared dryers and fluidized beds are known in the art for efficient drying of plant materials under appropriate conditions.

EXAMPLE 1

Materials and Methods

Plant Material and Sample Collection.

A proprietary spearmint line capable of rapid regrowth and accumulation of high RA levels was chosen for this study. Clones of this line were established at a greenhouse during winter months (November-January) under supplemental illumination. Samples for this study were taken by clipping the top 4-6 cm of the plants that were comprised of young new leaves with smaller stems. The initial fresh weight of each replicate of spearmint tissue sample used for different drying methods was 5±0.05 g.

Drying Methods:

Drying experiments were carried out using three different drying processes: conventional dehydrator, conventional microwave and freeze-dryer.

(a) Conventional dehydrator: Leaf tissue was dried using the standard vegetable dehydrator (Open Country—Sportsman Kitchen) in three replicates for each treatment. Pre-weighed leaf tissue was spread as a thin layer on the trays of the dehydrator. Three different drying temperatures in the dehydrator (35° C., 41° C. and 57° C.) were set for drying the tissue samples. In addition the tissue was also dried at room temperature (RT) as a control. The tissue for these four different temperatures was dried for 0 h, 24 h, 48 h, 72 h and 96 h. In total, 60 samples from three replicates of tissue dried at four different temperatures for five different time points were analyzed for the dehydrator process. Weights of each sample (post-treatment weights) were recorded for each treatment after drying for the set time and temperature. Relative water content in each sample after drying treatment was estimated as (post-treatment weight/pre-treatment weight)*100 and expressed as percentage (%).

(b) Microwave: A programmable domestic microwave oven (GE-JES1656SJ-02) with maximum output of 1150 W was used for the drying experiments. In each of the drying experiments, 5±0.1 g of leaf tissue was uniformly spread on the turntable inside the microwave cavity, and allowed to turn for an even absorption of microwave energy. Samples were dried for eight different time periods (30 sec, 1 min, 1 min 30 sec, 2 min, 2 min 30 sec, 3 min, 3 min 30 sec, 4 min) at a randomly chosen 70% output power. Three replications for each treatment were performed according to the preset microwave output power. Tissue samples after each time point of drying were weighed immediately. Relative water content after each treatment was estimated as (post-treatment weight/pre-treatment weight)*100 and expressed as %.

(c) Freeze drying: A research level freeze-dryer was used for drying the spearmint tissue. Three replicates of tissue (5±0.1 g) were lyophilized for 0 h, 24 h, 48 h, 72 h and 96 h. Tissue samples after each time point of drying were weighed immediately. Relative water content after each treatment was estimated as (post-treatment weight/pre-treatment weight)*100 and expressed as %.

Chemotyping:

Leaves from each sample from all the three drying experiment (that includes all treatments of dehydrator, microwave and freeze-drying and air-dried samples) were ground manually using pestle and mortar. A rapid method for RA quantitation using HPLC as described below was used for all samples. All the samples for each drying method were compared with each other within the drying experiment and also between the drying experiments.

Data Analysis:

Statistical analysis was performed on all data for each drying method separately using SAS 9.2. For the freeze drying and microwave drying method, the RA levels and weights for each treatment were analyzed by one way analysis of variance. A factorial design (temperature×duration) was used to analyze the dehydrator drying method. Fisher's least significant difference (LSD) obtained for each treatment and treatment combination was used to discriminate the means for comparison.

Rosmarinic Acid Quantitation

Chemicals and Reagents.

RA reference standard (99.0%) was obtained from Sigma-Aldrich (Cat. #53,6954). Acetonitrile, ethanol, water, and o-phosphoric acid (85%), were HPLC grade and acquired from Fisher Scientific.

Sample Preparation Method.

Spearmint plant tissue was harvested in January and dried via the drying parameters described above [0017]-[0020]. The leaf and small stem tissue were ground using a mortar and pestle. Accurately weighed ca 10.25±0.25 mg of freshly ground spearmint tissue was placed into a tared 2.0 mL microfuge tube. Accurately transferred 1.8 mL of extraction solvent (20 mM $KH_2PO_4$ (pH 2.5):ethanol (1:1 v/v)) was added to each tube and vortexed each for 1 minute. The 20 mM potassium phosphate solution ($KH_2PO_4$) was prepared by dissolving 0.680 g potassium phosphate monobasic (HPLC grade) into a beaker with ca 450 mL water (HPLC grade), adjusted to pH 2.5 with a few microliters of phosphoric acid, transferred to a 500 mL volumetric flask and topped to volume with water. The microcentrifuge tubes were partially immersed in a room temperature (approx. 22° C.) sonication bath (Fisher Scientific, Model FS60D with a fixed power setting) without tube closures becoming submerged. Tubes were sonicated for 10 minutes followed by an additional minute of vortexing. The tubes were placed in a microcentrifuge and pelleted for 10 minutes at 9600×g. A portion of each supernatant was transferred to a syringe with filter (0.245 µm PTFE, 25 mm diameter) and syringe-filtered into amber autosampler vials and sealed with crimp caps. It was observed with prior use of nylon syringe filters that RA recoveries were reproducibly decreased. Evaluation of same-sample aliquots filtered through either PTFE or nylon media revealed ca 10% RA retention to nylon, so PTFE filters must be used to assure quantitative recovery from aqueous RA samples.

Instruments and Conditions.

All chromatographic analyses were performed using a combination of Agilent 1100 and 1200 series HPLC modules with diode array detector, quaternary pump, autosampler, column heater, and online degasser. Data were analyzed using the HPLC ChemStation™ LC3D software. The column was a LiChrosorb RP-18 (250×4.6 mm, 5 µm, Supelco) with a C18 guard (Supelco) and PEEK coupler.

The mobile phase consisted of 0.1% o-phosphoric acid (Channel A) and 0.1% o-phosphoric acid in acetonitrile (Channel B). Mobile phase A was prepared by addition of 1.00 mL o-phosphoric acid to water in a 1-L volumetric flask, and adjusted to volume with water. Mobile phase B was prepared similarly with acetonitrile. The gradient program is tabulated in Table 1 with a constant flow rate of 1.0 mL/min, the column temperature maintained at 35° C., chromatograms were monitored at multiple wavelengths (quantification was at 330 nm only, cf. Wavelength Monitored), and injections were 5 µL.

TABLE 1

| HPLC elution program. | | | |
|---|---|---|---|
| Mobile phases | Channel A | 0.1% o-Phosphoric acid in water | |
| | Channel B | 0.1% o-Phosphoric acid in acetonitrile | |
| Column | LiChrosorb RP-18 (250 × 4.6 mm, 5 µm, Supelco) with C18 guard (Supelco) | | |
| Gradient | Time | % B | Flow rate (mL/min) |
| | 0 | 28.0 | 1.0 |
| | 7.00 | 40.6 | |
| | 7.20 | 100 | |
| | 8.20 | 100 | |
| | 8.30 | 28.0 | |
| | 10.00 | 28.0 | |
| Wavelength | | 330 nm | |
| Injection Vol. | | 5 µL | |
| Temperature | | 35° C. | |

Preparation of Standard Solutions.

To generate the calibration curve, a stock standard solution A with 1.502 mg/mL RA in 20 mM $KH_2PO_4$ (pH 2.5):ethanol (1:1 v/v) was prepared. A series of working calibration solutions were made from the stock standard solution as listed in Table 2 to provide a range of concentrations from 0.0300 to 1.50 mg/mL RA. The working calibration solutions were assayed by HPLC using the method described in Table 2. The series standard solutions were injected in triplicate. The calibration curve was used to quantitate samples and standards in this study.

TABLE 2

Preparation of working calibration solutions.

| Standard stock solution | Stock level | Stock solution added | Volume stock added (mL) | Final volume (mL) | Final concentration (mg RA/mL) |
|---|---|---|---|---|---|
| A | 8 | A | 25 | 25 | 1.50 |
| B | 7 | A | 5 | 10 | 0.751 |
| C | 6 | A | 4 | 10 | 0.601 |
| D | 5 | A | 3 | 10 | 0.451 |
| E | 4 | A | 2 | 10 | 0.300 |
| F | 3 | A | 1 | 10 | 0.150 |
| G | 2 | F | 4 | 10 | 0.0601 |
| H | 1 | F | 2 | 10 | 0.0300 |

Wavelength Selection.

RA sample standard was run per the method, the absorption spectrum recorded and evaluated for the optimal wavelength to be monitored.

Linearity of Standards.

The linearity of responses of standards at various levels was calculated based on the standard calibration data. A plot was generated using standard concentrations versus peak area responses, and to which the best-fit line was regressed without forcing through the origin. The concentration of RA ranged between 0.030 to 1.52 mg/mL.

Precision of Standards LC Analysis.

The precision of the standards analysis was determined by performing seven sequential injections of standard solution level 5, and the percent relative standard deviation was calculated based on the peak area response.

Accuracy of Standards Injections.

A level 4 standard was prepped and various injection volumes were analyzed and data regressed to the best-fit curve—linear data indicating correspondence with accuracy. Injection volumes ranged from 2.0 to 50 μl corresponding to RA masses of 0.61 to 15 μg, respectively.

Precision of Combined Sample Prep and LC Analysis.

The precision of the sample analysis was conducted using a composite (milled/homogenized) sample of plant tissue. Extracts were prepped as described, seven sequential injections were made, and the percent relative standard deviation was calculated for the peak area responses.

Spike Recovery.

An assessment of method accuracy was evaluated by spike recoveries. These were performed by preparing a stock solution of plant tissue extract with 0.343 mg RA/mL. Level 8 calibration standard stock solution was used to spike the spearmint extract solution at various levels. The two stock solutions were then mixed in varying proportions to cover the working range of RA (Table 3). Based on the assay results of the stock solution, the theoretical concentrations of the mixes were calculated and compared to the values obtained by the assay, and the percent differences between the theoretical and the observed concentrations were calculated.

TABLE 3

Proportions used to make spiked solutions.

| Sample | Sample Volume (mL) | Standard Volume (mL) | Theoretical [RA] (mg/mL) |
|---|---|---|---|
| 1 | 1.40 | 0.10 | 0.422 |
| 2 | 1.30 | 0.20 | 0.500 |
| 3 | 1.20 | 0.30 | 0.577 |
| 4 | 1.00 | 0.50 | 0.733 |
| 5 | 0.50 | 0.50 | 0.928 |

Peak Resolution.

Analyte resolution was evaluated using RA and neighboring peaks derived from the precision experiment data of real-matrix samples. Resolution was calculated by using Equation 1, where R was the resolution, $t_\#$ corresponded to the retention time of the peak, and $w_\#$ was the width of the peak in time units.

$$\text{(Resolution)}: \quad R = 2\frac{(t_2 - t_1)}{(\omega_2 + \omega_1)} \qquad \text{Equation 1}$$

Limits of Detection and Quantitation.

The standard calibration curve data were used to calculate the limits of detection and of quantitation. The detection limit was calculated according to Equation 2. The quantitation limit was calculated according to Equation 3. In these equations, s is the slope of the calibration curve, and σ is the residual standard deviation of the regression line, $\sigma=[(\Sigma \text{(residuals2)}/\text{degrees of freedom}]^{1/2}$, where the residuals are the difference of the observed and the best-fit values.

$$\text{(Limit of Detection)}: DL = 3.3\sigma \div s. \qquad \text{Equation 2}$$

$$\text{(Limit of Quantitation)}: QL = 10\sigma \div s \qquad \text{Equation 3}$$

Results

The initial moisture content of the fresh tissue tested using a moisture meter was approximately 87%. However, for the graphical representation of water loss over a period of time, the initial moisture levels were considered to be 100%. The moisture levels after each treatment was noted but the RA levels were not adjusted accordingly. The room temperature during the time of experiment was 22.2° C. and humidity was about 26%. The RA level for the 0 h time point (fresh tissue samples) for all drying methods was <2 mg/g. Since the estimated RA levels per unit sample weight in fresh tissue are diluted due to the high amounts of water present in them, these 0 h samples can bias the comparisons between drying time points. Therefore time point 0 h was not considered for the data analysis except for graphical representation.

Dehydrator Study:

The dehydrator study was performed independently during the same week as that of the other drying methods. The analysis of variance, drying curves and the RA levels from the dehydrator study are presented below.

(a) Analysis of variance: Significant variation was found for post-treatment weights and RA levels for both treatments (temperature and time) and treatment combinations (temperature×time) in this study (Table 4).

TABLE 4

Mean squares and P values for post-treatment weights and RA levels for samples dried using dehydrator.

| Source | Deg. of freedom | Post drying weights | | RA levels | |
|---|---|---|---|---|---|
| | | Mean squares | P value | Mean squares | P value |
| Rep | 2 | 0.01334 | 0.1362 | 73.037 | 0.0564 |
| Temp | 3 | 0.2269 | <0.0001 | 2651.54 | <0.0001 |
| Time | 3 | 0.1099 | <0.0001 | 233.01 | <0.0001 |
| Temp*Time | 9 | 0.0665 | <0.0001 | 329.54 | <0.0001 |
| R2 | | 0.897 | | 0.841 | |
| CV % | | 12.95 | | 27.24 | |

The means and LSDs of different temperatures are given in Table 5. Among different durations of drying, 24 h of drying was significantly different from other durations for post-treatment weights. RA levels were significantly lower in 24 h drying period and higher in 96 h drying period compared to all time points. Among different temperatures, post-treatment weight was significantly higher at RT while RA levels were significantly lower at 57° C. (Table 5).

The means and LSD of different temperature×time combinations are given in Table 6. Among different treatment combinations, drying at RT for 24 h and 48 h had significantly higher post drying tissue weights while drying at 57° C. for 96 h had resulted in significantly lower tissue weights (Table 6). There were no significant differences among post-drying weights for tissue dried at 35° C. or 41° C. for any number of hours of drying. For RA levels, drying at RT for 24 h and at 57° C. for 24 h, 48 h, 72 h and 96 h all resulted in significantly low amounts of RA retention in tissues compared to other temperatures. Drying tissues at RT for 72 h and 96 h resulted in significantly higher levels of RA retention compared to other temperatures. No significant differences among RA levels were observed for tissue dried at 35° C. or 41° C. for any duration of drying (Table 5).

TABLE 5

Means and LSD of treatements( temperature and time)

| | Treatment | Post-treatment weights (g)† | RA levels in post-treatment samples (mg/g) † |
|---|---|---|---|
| Time of drying | 24 h | 0.675a | 17.36a |
| | 48 h | 0.580b | 20.84ab |
| | 72 h | 0.565b | 21.98ab |
| | 96 h | 0.564b | 23.14c |
| | LSD | 0.151 | 4.82 |
| Temperature | RT | 0.813a | 26.94a |
| | 35° | 0.565b | 25.62a |
| | 41° | 0.558b | 26.43a |
| | 57° | 0.507b | 4.62b |
| | LSD | 0.133 | 4.71 |

† Means with different letters are significantly different from each other

TABLE 6

Means and LSD of treatement (temperature × time) combinations.

| Treatment combination | Post-treatment weights (g) † | RA levels in post-treatment samples (mg/g) † |
|---|---|---|
| RT_24 h | 1.273a | 1.25a |
| RT_48 h | 0.747b | 29.07bcd |
| RT_72 h | 0.640bcd | 35.19d |
| RT_96 h | 0.593cde | 33.67cd |

TABLE 6-continued

Means and LSD of treatement (temperature × time) combinations.

| Treatment combination | Post-treatment weights (g) † | RA levels in post-treatment samples (mg/g) † |
|---|---|---|
| 35°_24 h | 0.657bc | 26.39b |
| 35°_48 h | 0.543cde | 27.06bc |
| 35°_72 h | 0.533cde | 24.66b |
| 35°_96 h | 0.527cde | 24.40b |
| 41°_24 h | 0.540cde | 29.58bcd |
| 41°_48 h | 0.557cde | 22.95b |
| 41°_72 h | 0.553cde | 24.48b |
| 41°_96 h | 0.583cde | 28.73bcd |
| 57°_24 h | 0.543cde | 4.92a |
| 57°_48 h | 0.470e | 4.22a |
| 57°_72 h | 0.510de | 3.58a |
| 57°_96 h | 0.503e | 5.77a |
| LSD | 0.136 | 6.87 |

Figure 1B:
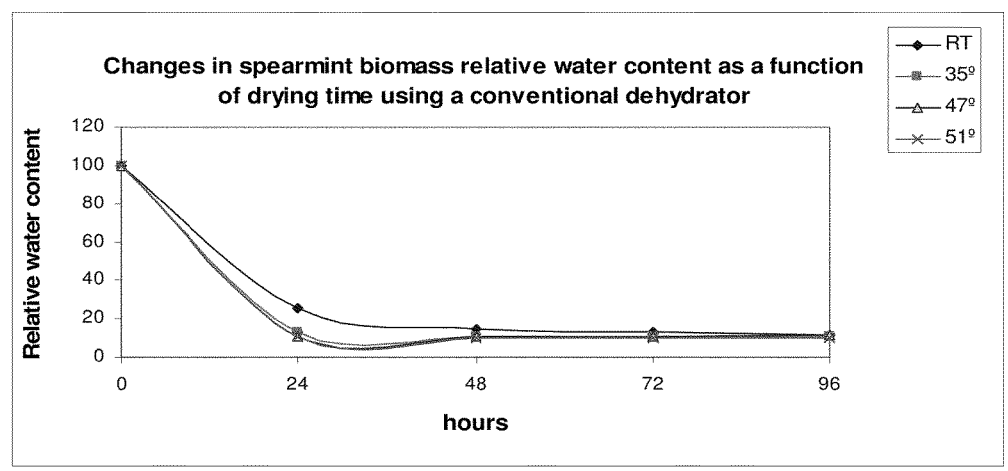

† Means with different letters are significantly different from each other (b) Drying curve: The variation of post-treatment weight of the tissue as a function of time was followed. Plots of the relative moisture content as a function of time and rate of drying are shown in FIG. 1. Thus an experimental curve representing the drying characteristics of spearmint tissue was obtained. The post-treatment weights of spearmint tissue in relation to drying time are presented in FIG. 1a and the changes in relative water content as a function of drying time is given in FIG. 1b. The relative water content dropped from 100% to 15% at RT in 48 hours and then gradually reached 10% level in 96 h. On the other hand while drying at 35° C., the relative water content dropped to 13% at 24 h and reached 10% after 48 h and remained constant for the rest of the time. However, at 41° C. and 57° C. the relative water content rapidly dropped to 10% within 24 h of drying and remained constant for the rest of the drying durations.

The time taken to reach a moisture content of about 10% at RT was about 48 h, while it took only about 24 h using a dehydrator set at 35° C., 41° C. and 57° C. The moisture content remained at a constant level of 10% whether dried at RT, 35° C., 41° C. or 57° C. after 48 h (FIGS. 1a and 1b).

Figure 2:
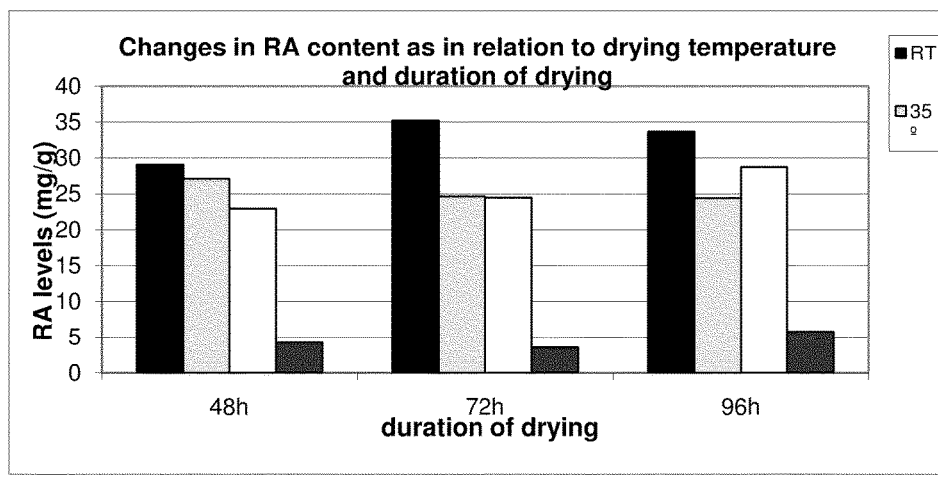
FIG. 2 is a graph of the effect of temperature and duration of drying on RA content using the dehydrator.

(c) RA levels: The effect of temperature and duration of drying on RA content of spearmint tissue dried using dehydrator is given in FIG. 2. The highest level of RA was retained when the tissue was dried at RT for 48 h-72 h after which the RA levels gradually started to decrease. The RA levels of tissue dried at 35° C. and 41° C. remained at a relatively constant level while dried for 48 h, 72 h and 96 h. However the tissue dried at 57° C. lost most of the RA content (about 80% lost) when dried for 24 h or greater.

Microwave Study:

The microwave study was performed independently during the same week as that of the other drying methods study. The analysis of variance, drying curves and the RA levels from the microwave study are presented below.

(a) Analysis of variance: The analysis of variance showed significant variation for post-treatment weights and RA levels for eight different durations of microwave drying in this study (Table 7).

TABLE 7

Mean squares and P values for post-treatment weights and RA levels for samples dried using microwave.

| Source | df | Post-treatment weights Mean squares | P value | RA levels Mean squares | P value |
|---|---|---|---|---|---|
| Rep | 2 | 0.0276 | 0.4702 | 64.42 | 0.6889 |
| Time | 7 | 0.406 | <0.001 | 2901.65 | <.0001 |
| R2 |  | 0.857 |  | 0.849 |  |
| CV % |  | 20.30 |  | 19.48 |  |

The means and LSD for the duration of drying are given in Table 8. Among different durations of drying, 0.5 min of drying was significantly different from all other durations and 1 minute of drying was significantly different from ≥2.5 minutes of drying for post-treatment weight. RA levels were significantly lower in 0.5 min and 4 min microwave drying and significantly higher for the rest of the time points. Among all time points, 2.5 minutes of drying seem to retain the highest amount of RA with minimal tissue shrinkage (Table 8).

TABLE 8

Means and LSD for post treatement weights and RA levels for microwave study

| Duration of drying | Post-treatment weights (g)† | RA levels in post-treatment samples (mg/g)† |
|---|---|---|
| 0.5 | 1.720a | 13.54a |
| 1 | 1.167b | 34.38b |
| 1.5 | 0.900bc | 58.69c |
| 2 | 0.797bc | 67.80cd |
| 2.5 | 0.793c | 74.59d |
| 3 | 0.697c | 68.43cd |
| 3.5 | 0.677c | 67.59cd |
| 4 | 0.603c | 35.25b |
| LSD | 0.326 | 11.99 |

Figure 3:
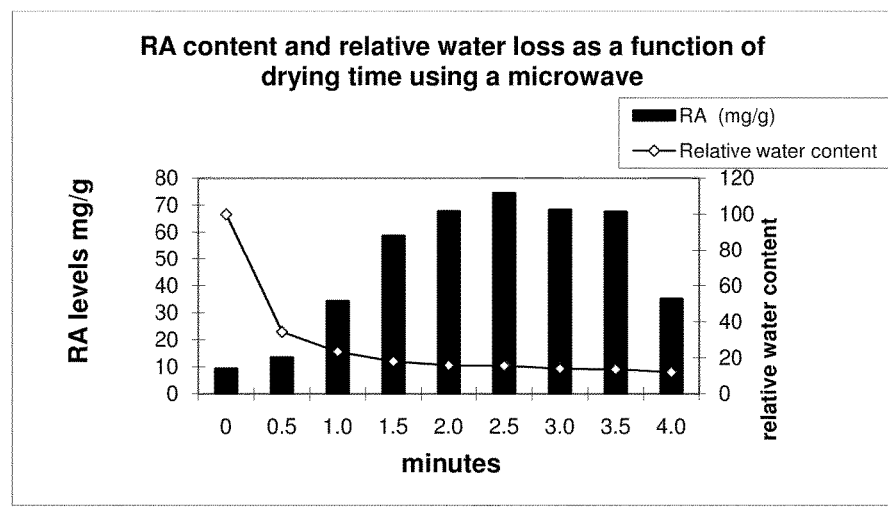
FIG. 3 is a graph of relative water content and RA levels as a function of sample weight during microwave drying.

†Means with different letters are significantly different from each other (b) Drying curve and RA levels: The relative water content and RA levels versus duration of drying curves for microwave drying at 70% microwave output power of spearmint tissue is shown in FIG. 3. A rapid decrease in moisture content in the tissue was observed wherein the moisture levels dropped from 100% to 30% in 30 seconds. The microwave drying process reduced the spearmint tissue moisture content to approximately 15% in 2.5 minutes. As the duration of drying increased from 2.5 min up to 4 minutes there was no further significant reduction in moisture levels in the tissue. The highest level of RA was observed at 2.5 minutes of microwave drying which was significantly higher than all other durations tested. The RA levels gradually increased with an increase in duration of drying up to 2.5 minutes and then gradually decreased with the increase in time.

Freeze-Dryer Study:

The freeze dryer study was performed independently during the following week of the dehydrator and microwave study. The analysis of variance, drying curves and the RA levels from the freeze-dryer study are presented below.

(a) Analysis of variance: The analysis of variance showed no significant variation for both post-treatment weights and RA levels for four different durations of freeze-drying (Table 9).

TABLE 9

Mean squares and P values for post-treatment weights and RA levels in freeze-dryer study.

| Source | df | Post-treatment weights Mean squares | P value | RA levels Mean squares | P value |
|---|---|---|---|---|---|
| Rep | 2 | 0.0225 | 0.2667 | 160.40 | 1.79 |
| Time | 3 | 0.0567 | 0.0643 | 188.132 | 0.2335 |
| R2 |  | 0.865 |  | 0.878 |  |
| CV % |  | 20.1 |  | 16.71 |  |

The means and LSD for the duration of drying are given in Table 10. Among different durations of drying, 24 h of drying was significantly different from all other time points for post-treatment weights. However the RA levels did not vary for different durations of freeze-drying. Among all time points, 24 h of freeze drying seem to retain the highest amount of RA with the lowest amount of tissue shrinkage (Table 10).

TABLE 10

Means and LSD for post treatement weights and RA levels for freeze-dryer study

| Duration of drying | Post-drying weights (g)† | RA levels (mg/g)† |
|---|---|---|
| 24 h | 1.026a | 79.89a |
| 48 h | 0.760b | 63.16a |
| 72 h | 0.757b | 64.86a |
| 96 h | 0.740b | 64.36a |
| LSD | 0.233 | 19.50 |

Figure 4:
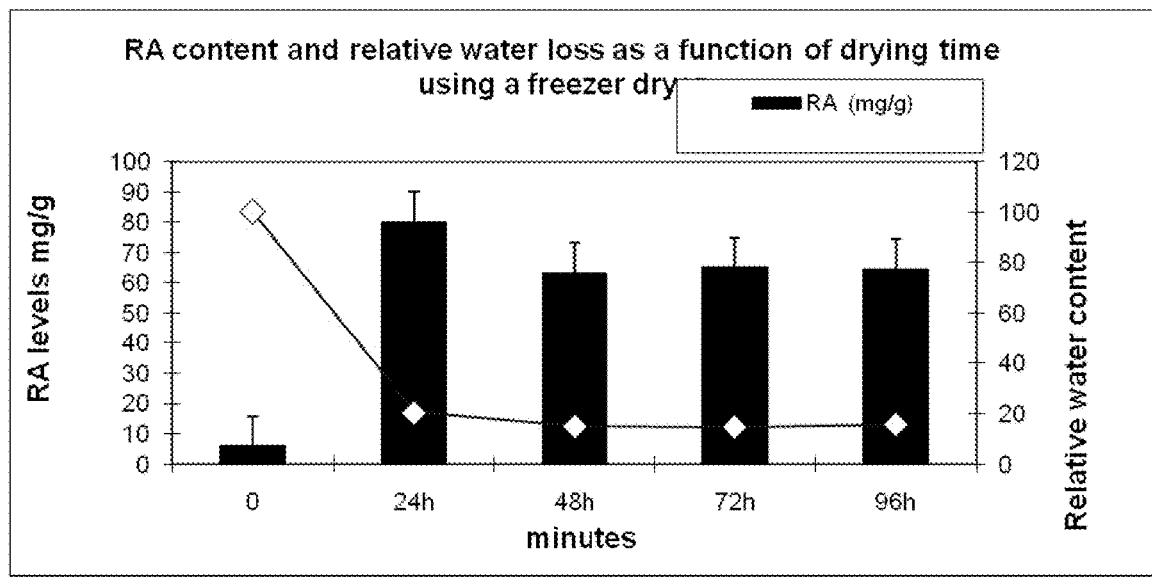
FIG. 4 is a graph of relative water content and RA levels as a function of sample weight during freeze-drying.

†Means with different letters are significantly different from each other (b) Drying curve and RA levels: The relative water content and RA levels versus duration of drying curves for freeze drying of spearmint tissue is shown in FIG. 4. A rapid decrease in moisture content in the tissue was observed where the moisture levels dropped from 100% to 20% in 24 h of freeze drying and remained at a constant of <15% for further time points. There was no significant change in RA levels irrespective of duration of drying.

Discussion

Spearmint is a highly seasonal and perishable plant with high levels of moisture content. KI-MsEM0028 had initial moisture content of 87±0.5%, which indicates that 870 kg water have to be evaporated per 1000 kg of fresh mint leaves before extraction.

The results from the dehydrator study suggested that the temperature at which the tissue was dried and the duration of drying played a significant role in rapid loss of moisture and retention of the RA levels. Results showed that drying took place rapidly during the first 48 hours of drying treatment where the moisture levels dropped from 100% to less than 20%. This was followed by a relatively constant drying period where the relative water content lowered from approximately 15% to 10% at RT and remained constant at about 10% for the other temperatures. However, the RA levels seem to be retained at the highest level after drying at RT for 48 h to 72 h. Although a faster process, drying tissues at temperatures higher than RT using a dehydrator reduced the RA levels below 30 mg/g. The RA levels when dried at 35° C. or 41° C. remained constant after drying for 48 h or greater. However, when the tissue samples were dried at higher temperature (≥57° C.) the RA levels were reduced by up to 80% within 24 h of drying. The length of time required to dry the leaf tissue using a conventional drying approach would be too long for commercial utility. Furthermore, as RA level and stability is highly temperature sensitive, drying would be limited to temperatures below 41° C.

In microwave drying, different durations starting from 30 sec to 4 minutes were used for drying the tissue. A maximum of 4 minutes drying was adopted beyond which browning of tissue became an issue. There was a rapid reduction in moisture levels to a 30% moisture level within 30 sec of drying at 70% output power. The optimum drying time for maintaining highest RA levels without much tissue shrinkage was about 2.5 minutes wherein the moisture levels were about 10%.

Freeze drying retained the highest levels of RA after 24 h of drying with the lowest amount of tissue shrinkage observed. A rapid reduction in moisture level was observed at 24 h of drying after which the moisture levels remained at a constant level. However, continuous freeze-drying of tissue beyond an optimum level of 24 h did not significantly reduce the RA levels as observed with the dehydrator and microwave methods.

In comparing all three methods, the microwave method dried the tissue faster without significant reduction in the RA levels, leaf color and tissue shrinkage. Although freeze drying seems to be the most efficient in terms of retention of RA levels, it requires much more capital investment and time for drying which limits its utility at a commercial scale. In summary, microwave drying is a surprisingly effective method for drying the spearmint biomass while maintaining optimum RA levels for extraction.

EXAMPLE 2

Approximately 2.5 acres each of the 2 proprietary rosmarinic acid (RA) hyper-accumulator spearmint clonal lines (KI-MsEM0110 and KI-MsEM0042) were grown at two field locations. A pilot scale microwave dryer was assembled and transported to the fields for drying of the spearmint plant material shortly after harvesting. The microwave dryer system included two 75 kilowatt transmitters with wave guides two oven units which included variable speed top and bottom conveyor belts to hold the spearmint leaf and stem tissue as it passed through the ovens (AMTek, Cedar Rapids, Iowa).

Spearmint leaf and stem tissue was harvested in the field using a windrower (John Deere 3430) and manually lifted into a wagon for transportation to the microwave dryer system, situated in a farm building. Belt load, energy level and belt speed were varied until leaf and stem tissue reached a moisture level <10% and arcing occurrence was minimized.

Composite samples of leaf and stem tissue were also taken at the same time for drying in a small household microwave oven for comparison purposes. Three replicate samples of each composite were tested for RA content using the described in Example 1. Samples of whole leaf and chopped leaf were taken for a comparison of RA stability over time post-harvest.

Preferred settings for KI-MsEM0110 were an energy level of 63 KW in oven 1; 15 KW in oven 2; and a belt speed of 40"/minute to achieve a consistently dry product <10% moisture. The power used to remove each pound of water at the preferred settings was 0.392 kwh/lb (40,671 BTU/30 lbs=1,356 BTU/lb/3412.3 kw/BTU).

Rosmarinic acid levels ranged from approximately 5.0% to >7.0% on a dry matter basis which was favorable considering that harvest and drying occurred post flowering. These levels would be expected to be >9.0% when harvested pre-flowering. There were no significant differences in rosmarinic acid levels between the control microwave-dried tissue and the tissue dried in the larger scale pilot microwave system. It is important that whole leaf tissue be harvested as a rapid loss of rosmarinic acid was observed in chopped leaf tissue compared to whole leaf tissue.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

We claim:

1. A method of drying harvested plant material to reduce the weight and volume of plant material by removing water from tissue of a mint plant containing rosmarinic acid without degrading the majority of the rosmarinic acid content in the plant tissue, the method comprising:
   (a) using at least one microwave chamber;
   (b) placing the plant tissue on a conveyor, moving the plant tissue on said conveyor through the microwave chamber; and
   (c) exposing the plant tissue to energy at an intensity by adjusting the conveyor load, microwave energy level and conveyor speed sufficiently to remove water from the plant tissue to a stable moisture level of 10% or less upon exit from the microwave chamber; wherein the method retains rosmarinic acid for year-round extraction without degrading the majority of the rosmarinic acid content of the tissue of the mint plant.

2. A method as defined in claim 1, wherein the intensity is between 0.001 W/cm3 and 1.0 W/cm3.

3. A method as defined in claim 2, wherein the time is between 5 seconds and 250 seconds.

4. A method for drying harvested plant material to reduce the weight and volume of plant material while preserving a majority of the rosmarinic acid content in the plant material, the method comprising:
   a. placing at least one microwave substantially at a growing location, the microwave further comprising a microwave chamber and a conveyor;
   b. harvesting fresh plant material from a growing mint plant;
   c. within 24 hours of harvesting of the fresh mint plant material, placing the plant tissue on the conveyor, moving the plant tissue on said conveyor through the microwave chamber, and exposing the fresh mint plant material to microwave energy at an intensity by adjusting the conveyor load, microwave energy level and conveyor speed sufficient to remove water from the fresh mint plant tissue to a stable moisture level of 10% or less upon exit from the microwave chamber without degrading a majority of the rosmarinic acid to produce dried plant material; and
   d. separating the rosmarinic acid from the dried plant material, whereas the separating can occur year-round.

5. A method as defined in claim 4, wherein the intensity is between 0.001 W/cm3 and 1.0 W/cm3.

6. A method as defined in claim 5, wherein the time is between 5 seconds and 250 seconds.

7. A method as defined in claim 1, wherein the rosmarinic acid content of the mint plant tissue before drying is less than 2 mg/g and the rosmarinic acid content of the mint tissue after drying is between 5% and 9%.

8. A method as defined in claim 4, wherein the rosmarinic acid content of the mint plant tissue before drying is less than 2 mg/g and the rosmarinic acid content of the mint tissue after drying is between 5% and 9%.

9. A method for drying a harvested mint plant to reduce the weight and volume of plant material by drying fresh plant material with an on-site dryer in order to retain rosmarinic acid content for later extraction, the method comprising:
   a. placing at least one drying apparatus substantially on-site, near a field growing plant material, the drying apparatus further comprising at least one dryer unit and at least one belt unit;
   b. harvesting the fresh plant material;
   c. placing the fresh plant material on the belt unit for passage through the dryer unit; and
   d. drying the fresh plant material after harvesting by exposing the plant material to energy to remove water from the plant tissue to a stable moisture level of 10% or less upon exit from the dryer unit without degrading a majority of the rosmarinic acid content of the tissue of the mint plant;
wherein the method is performed at ambient pressure.

10. The method of claim 9, wherein the plant tissue is whole leaf tissue.

11. The method of claim 10, wherein the dryer unit further comprises at least variable speed top and bottom conveyor belts.

12. The method of claim 9, wherein the drying apparatus is selected from the group consisting of a microwave, a freeze dryer, an infrared dryer, and a fluidized bed.

13. The method of claim 9, wherein the plant material is spearmint.

14. The method of claim 13, wherein the material is exposed to energy between 0.001 W/cm3 and 1.0 W/cm3.

15. The method of claim 14, wherein the material is exposed to energy for between 5 seconds and 250 seconds.

16. The method of claim 15, wherein the rosmarinic acid content of the plant tissue before drying is less than 2 mg/g and the rosmarinic acid content of the tissue after drying is between 5% and 9%.

17. The method of claim 1, wherein the method occurs at ambient pressure.

18. The method of claim 1, wherein the method occurs at less than 57° Celsius.

19. The method of claim 18, wherein the method occurs at less than 41° Celsius.

20. The method of claim 4, wherein the method occurs at ambient pressure.

21. The method of claim 4, wherein the method occurs at less than 57° Celsius.

22. The method of claim 9, wherein the method occurs at less than 57° Celsius.

* * * * *